US008939982B2

(12) United States Patent
Chellaoui (10) Patent No.: US 8,939,982 B2
(45) Date of Patent: Jan. 27, 2015

(54) METHODS AND DEVICES FOR VALIDATING THE POSITION OF PATIENT-SPECIFIC DEVICES

(75) Inventor: Karim Chellaoui, Rue de Namur (BE)

(73) Assignee: Materialise N.V., Leuven (BE)

( * ) Notice: Subject to any disclaimer, the term of this patent is extended or adjusted under 35 U.S.C. 154(b) by 671 days.

(21) Appl. No.: 13/106,448

(22) Filed: May 12, 2011

(65) Prior Publication Data

US 2012/0290019 A1    Nov. 15, 2012

(51) Int. Cl.
A61B 17/56 (2006.01)
A61F 2/46 (2006.01)
A61B 17/15 (2006.01)
A61B 17/17 (2006.01)
A61F 2/30 (2006.01)
A61B 19/00 (2006.01)

(52) U.S. Cl.
CPC .............. *A61F 2/4607* (2013.01); *A61F 2/461* (2013.01); *A61B 17/157* (2013.01); *A61B 17/175* (2013.01); *A61B 2017/568* (2013.01); *A61F 2/30942* (2013.01); *A61B 2019/502* (2013.01); *A61F 2002/4687* (2013.01)
USPC ...................................... 606/86 R; 606/86 B (58) Field of Classification Search
USPC .......... 606/53, 60, 86 B, 86 R, 87–89, 96–97, 606/99, 86 A, 104, 130, 281
See application file for complete search history.

(56) References Cited

U.S. PATENT DOCUMENTS

| 3,727,611 | A  | * | 4/1973 | Schultz ........................... 606/96 |
| 5,423,832 | A  |   | 6/1995 | Gildenberg |
| 8,092,465 | B2 | * | 1/2012 | Metzger et al. ................. 606/96 |
| 8,444,651 | B2 | * | 5/2013 | Kunz et al. ...................... 606/87 |
| 8,652,180 | B2 | * | 2/2014 | Federspiel et al. ............ 606/281 |
| 2009/0254093 | A1 | * | 10/2009 | White et al. ..................... 606/89 |
| 2010/0286700 | A1 | * | 11/2010 | Snider et al. .................... 606/89 |

FOREIGN PATENT DOCUMENTS

| FR | 2758256 A1 | 7/1998 |
| GB | 2391814 A | 2/2004 |
| WO | 2004075716 A2 | 9/2004 |
| WO | WO 2010102247 A2 * | 9/2010 ............. A61B 17/90 |

OTHER PUBLICATIONS

Intl. Search Report issued Aug. 7, 2012 on related application PCT/EP2012/058716 filed May 11, 2012.
International Preliminary Report on Patentability and Written Opinion of the International Searching Authority dated Nov. 12, 2013 on related application PCT/EP2012/058716 filed May 11, 2012.

* cited by examiner

*Primary Examiner* — Nicholas Woodall
*Assistant Examiner* — Larry E Waggle, Jr.
(74) *Attorney, Agent, or Firm* — EIP US LLP (57) ABSTRACT

The present invention relates to methods for validating the correct position of a patient-specific device on a chosen anatomy of the human body as well as such patient-specific devices. More specifically, the devices are provided with a fitting tool which allows in alignment of the patient-specific device with one or more predetermined patient-specific landmarks.

14 Claims, 8 Drawing Sheets

METHODS AND DEVICES FOR VALIDATING THE POSITION OF PATIENT-SPECIFIC DEVICES

FIELD OF THE INVENTION

The present invention relates to tools and methods for validating the correct position of a patient-specific device on a chosen anatomy of the human body as patient-specific devices comprising such tools.

BACKGROUND OF THE INVENTION

Conventional orthopedic implants such as knee and hip implant systems have been in use for many years with considerable success. The use of custom designed implant components based on the patient-specific anatomy has moreover overcome many shortcomings of the older designs. Such patient-specific devices can be developed using commercially available software. Typically such devices are used for orthopedic interventions to the spine, hip, knee and/or radius. Patient-specific devices available on the market include patient-specific knee replacement prostheses, patient-specific femoral and tibial cutting blocks, distal radius drilling and cutting templates.

While patient-specific guides are now typically used to accurately place pins, guide bone cuts or insert implants during orthopedic procedures, the correct positioning of these patient-specific devices remains a critical factor with important impact on the outcome of the procedure.

Patient-specific devices are made according to a pre-operative plan formed from an MRI or CT scan of the patient and rely on the matching of an anatomical feature for correct positioning. Typically they contain at least one surface which mates specifically with the surface of the bone. They further contain one or more functional elements such as cylinders which guide the orientation of a drill or pin in the correct predetermined position in the bone.

While finding the correct position of the patient-specific devices may seem straightforward as the operator only needs to determine the correct patient-specific fit, it has often been observed that, minor discrepancies from the perfect fit will not be perceived by the operator. There are many causes for this, one of the most important being the presence of soft tissue which has not been entirely removed from the bone. The actual placement of the patient-specific device in the correct position is therefore not always that straightforward for the operator, leading to uncertainty for the operator and the possible incorrect placement of the patient-specific device, resulting in deviations from the surgical planning. As the best orthopedic results are achieved when the procedure occurs under the best circumstances, i.e. including not only the device being correctly positioned but also the operator being assured about the correct position of the patient-specific device, there is a need in the art for devices which allow to ensure that a patient-specific device is positioned correctly.

The present invention aims at providing methods and devices that make it possible to ensure the correct position of a patient-specific device, without a major additional burden for the operator during surgery.

SUMMARY OF THE INVENTION

The present invention relates to methods and tools for validating the correct position of a patient-specific device on a chosen anatomy of the human body. More specifically, the invention relates to improved patient-specific devices which in addition to at least a patient-specific element further comprise a fitting tool which allows alignment of the patient-specific device with the user's line of sight or with the direction the image is taken by a medical imaging apparatus, and then allows alignment of the device with one or more predetermined patient-specific landmarks. When the patient-specific device is fitted onto the bone in the correct position, the alignment of the fitting tool with the user's line of sight or with the medical imaging apparatus should ensure the alignment of the fitting tool with predetermined patient-specific landmarks, so as to allow the operator to be assured that the patient-specific device is positioned correctly. An incorrect fit will accordingly lead to the fitting tool not being aligned with the predetermined patient-specific landmarks, when the fitting tool is aligned with the imaging apparatus and/or with the line of sight of the user.

The present invention relates to methods for validating the correct position of a patient-specific device on a chosen anatomy of the human body, the method comprising the steps of:

positioning said patient-specific device on said chosen anatomy of the human body, wherein said patient-specific device comprises;
(a) a patient-specific surface being complementary with at least part of the body or bone structure of said patient; and;
(b) a fitting tool comprising supporting means for connection of said fitting tool to said patient-specific device and
(i) at least one functional alignment element, for correctly aligning said device with the user's line of sight or with a medical imaging apparatus, and
(ii) one or more patient-specific landmarking elements, which line up with one or more predetermined patient-specific landmarks on said chosen anatomy when said device is in said correct position;
aligning said functional alignment element with the user's line of sight or with a medical imaging apparatus while maintaining said device in said position on said chosen anatomy; and
checking whether said one or more patient-specific landmarking elements line up with said predetermined patient-specific landmark on said chosen anatomy, thereby validating the correct position of a patient-specific device on a chosen anatomy of the human body.

More particularly, methods are provided wherein one or more of said predetermined patient-specific landmarks on said chosen anatomy is a crest, a concavity, a convexity, a peak or a tuberosity on the outline of a bone.

More particularly, methods are provided wherein at least one of said patient-specific landmarking elements is longitudinal and, when correctly positioned lines up with a specific point on a patient-specific landmark.

More particularly, methods are provided wherein at least one of said patient-specific landmarking elements, when correctly positioned lines up with part of the contour of said chosen anatomy (such as a bone) or of a part or feature thereof.

More particularly, methods are provided wherein at least one of said patient-specific landmarking elements, when the device is correctly positioned, lines up with an axis parallel or perpendicular to said chosen anatomy.

More particularly, methods are provided wherein the step of aligning said functional alignment element with the user's line of sight and/or with a medical imaging apparatus comprises aligning the direction of the image and/or the direction of sight with the direction of said alignment feature.

More particularly, methods are provided wherein the step of checking whether said patient-specific landmarking element lines up with said predetermined patient-specific landmark performed by imaging said device using a radiographic scan and/or an ultrasound scan.

The present invention also relates to patient-specific surgical, therapeutic or diagnostic devices, comprising a patient-specific surface, said patient-specific surface being complementary to least part of the body or bone structure of a patient, and further comprising a fitting tool for ensuring the correct fit of said device onto the chosen anatomy of the human body, i.e. checking whether the device is placed in the correct, i.e. desired position. More specifically, said fitting tool comprises supporting means for connection of said fitting tool to said patient-specific device and
(i) at least one functional alignment element, for correctly aligning said device with the user's line of sight and/or with a medical imaging apparatus when the device is positioned on the bone, and
(ii) one or more landmarking elements which, when said device is in said correct position, line up with one or more predetermined patient-specific landmarks on said chosen anatomy.

More particularly, patient-specific devices are provided wherein said fitting tool, is an integrated part of said patient-specific device.

In particular embodiments, patient-specific devices are provided wherein said fitting tool is removable from said patient-specific device.

More particularly, patient-specific devices are provided wherein said patient-specific landmarking element(s) and/or said functional alignment element are laser generating devices, positioned such that the generated laser beam can be used for correctly aligning said device with the user's line of sight or with a medical imaging apparatus and/or lines up with said patient-specific landmark(s).

More particularly, patient-specific devices are provided wherein said patient-specific landmarking element(s) and/or said functional alignment element are at least partially made from a radio-opaque material.

More particularly, patient-specific devices are provided additionally comprising means such as tunnels, loops, slots or dents for providing additional functionalities onto said device.

The present invention also relates to methods for manufacturing the patient-specific device comprising a fitting tool according to the invention. More particularly, said methods comprise the steps of:
obtaining patient-specific information regarding the chosen anatomy of the human body onto which the patient-specific device is to be positioned;
using said patient-specific information for designing said patient-specific device such that said device is provided with:
(a) a patient-specific surface being complementary with at least part of the body or bone structure of said patient; and;
(b) a patient-specific fitting tool comprising supporting means for connection to said patient-specific device and
(i) at least one functional alignment element, for correctly aligning said device with the user's line of sight and/or with a medical imaging apparatus when it is positioned on the chosen anatomy, and
(ii) one or more patient-specific landmarking elements, which line up with one or more predetermined patient-specific landmarks on said chosen anatomy when said device is in said correct position; wherein the position of said landmarking elements with regard to said functional alignment element is patient specific; and
manufacturing said patient-specific device.

More particularly, manufacturing methods are provided wherein the step of obtaining patient-specific information comprises performing a radiographic scan, a MRI scan and/or a CT scan.

More particularly, manufacturing methods are provided wherein said manufacturing step is ensured by additive manufacturing.

These and further aspects and embodiments are described in the following sections and in the claims.

BRIEF DESCRIPTION OF THE FIGURES

FIG. 1 represents a patient-specific device according to a specific embodiment of the present invention.
FIG. 2 represents a patient-specific device according to a specific embodiment of the present invention.
FIG. 3 represents a patient-specific device according to a specific embodiment of the present invention.
FIG. 4 represents a patient-specific device according to a specific embodiment of the present invention.

LIST OF REFERENCE NUMERALS USED IN THE FIGURES (1) Anatomical part; (2) Patient-specific device; (3) Fitting tool; (4) Patient-specific landmarking elements; (5) Functional alignment element; (6) Pre-identified landmarks; (7) Hand holders; (8) Specific contour patient-specific landmarking element; (9) Specific ring shaped the patient-specific landmarking element; (10) Specific patient-specific landmarking element.

Each of these illustrations represents particular embodiments of the features concerned and the corresponding features are not to be interpreted as limited to this specific embodiment.

DETAILED DESCRIPTION OF THE INVENTION

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The present invention relates to methods and tools for validating the correct position of a patient-specific device on a chosen anatomy of the human body. More specifically, the invention relates to improved patient-specific devices which in addition to at least a patient-specific element further comprise a fitting tool which, after the device has been placed on the chosen anatomy, allows on the one hand alignment of the patient-specific device with the user's line of sight and/or with a medical imaging apparatus, and secondly allows alignment of the device with one or more predetermined patient-specific landmarks. When the patient-specific device is fitted onto the bone in the correct position, the alignment of the fitting tool with the user's line of sight or with the medical imaging apparatus (whereby its position on the bone is maintained) should ensure the alignment of the fitting tool with predetermined patient-specific landmarks, so as to allow the operator to be assured that the patient-specific device is positioned in the correct (i.e. pre-operatively determined) way. An incorrect fit will accordingly lead to the fitting tool not being aligned with the predetermined patient-specific landmarks, when the fitting tool is aligned with the user's line of sight and/or the imaging apparatus.

As used herein, the term "patient-specific device" relates to any surgical, therapeutic or diagnostic devices or tools such as an implant or a guide which is designed based on an individual patient's anatomy to include features which have a custom fit or perform a customized function for a specific location in a specific patient. The use of patient-specific guides and implants allows to ensure an improved or optimized accuracy of the surgical intervention and an improved anatomical fit for prosthetic structures so as to ensure optimized functionality for each patient. Even when such devices are used in combination with standard implants, tools, devices, surgical procedures, and/or other methods important benefits in accuracy of placement can be obtained. It should further be noted that whereas the teaching of the present invention is mainly focused on using the invention with custom limb bone implants or guides, the present invention can also be applied for any type of patient-specific device that requires accurate positioning on any type of organic tissues such as bone, teeth, cartilage or skin. Accordingly, the term "patient-specific device" is used to refer to a custom-made device specific to the individual patient's anatomy. Therefore the device is a device comprising at least one surface which conforms or is complementary with at least part of the patient's anatomy. The complementary surface is also referred herein as the "patient-specific element". Devices comprising one or more patient-specific elements are known from the art.

The devices according to the invention are characterized in that they are provided with a fitting tool. The term "fitting tool" as used herein relates to an element positioned on the patient-specific device or reversibly linked thereto which comprises at least one functional alignment element and one or more patient-specific landmarking elements.

The functional alignment element or elements are used to ensure the correct position of the patient-specific device with regard to the direction the image is taken. Thus this is used to indicate in which position the patient-specific device should be visualized by the user or a medical imaging apparatus in order to be able to assess the correct position of the device on the patient (based on the matching between the patient-specific landmarking elements and the landmarks on the intra-operative modality.

Thus, based on the alignment element(s) the position of the device in relation to the viewpoint of the user or the medical imaging apparatus is adjusted as to allow the user to correctly assess whether the patient-specific device is positioned in the correct position.

The patient-specific landmarking element or elements are used to determine the correct position of the patient-specific device relative to the patient. These allow to assess the correlation between the relative position of the device and the identified landmarks on the planning modality and the relative position of the device and the corresponding landmarks on the intra-operative modality.

It should be noted that the fitting tool can be regarded either as a one-piece element positioned on the patient-specific device integrating the landmarking elements and the functional alignment elements, or as a cluster of separate elements positioned individually on the patient-specific device, whereby each of the individual elements can function as patient-specific landmarking elements, functional alignment elements or both.

As used herein, the term "patient-specific landmark" relates to a feature of which the presence, size or shape is specific for the patient's anatomy, and which is identifiable in the imaging modality that is used to establish the surgical planning, referred in the description as the "planning modality" as well as in the imaging modality that is used intra-operatively, also referred to as the "intra-operative modality".

The anatomical landmarks envisaged in the context of the present invention can be of any shape and size and are chosen depending on the specific configuration of the patient. Examples of such anatomical landmarks can be but are not limited to points, lines, planes, circles, crests, intersections between curves, convexity, cavities . . . . They should be identifiable by the user in both the planning and intra-operative modalities. The selection of the landmarks depends on the intended use, and on the characteristics of the used imaging modalities such as depth of scan, contrast levels, visibility of tissues, distance to the fitting device, etc. A landmark can be any shape recognizable by the user on images to allow pattern correlation. These landmarks can be plainly visible (e.g. angular points or lines) or can be deducted by the user (e.g. the main axis of a longitudinal shape, parallel or perpendicular lines). Because the same landmarks can appear differently depending on the used imaging modality a specific landmark needs to be defined in a specific way when viewed in a given imaging modality.

The definition of a landmark solely depends on the ability of the user to identify the landmark in a given modality. An example of this can be given for bone tissues that can be displayed in white when viewed on a CT scan but can appear in black on a MRI scan. Planning modalities can be conventional methods of X-ray imaging and processing, X-ray tomosynthesis, ultrasound including A-scan, B-scan, C-scan, computed tomography (CT scan), magnetic resonance imaging (MRI), optical coherence tomography, single photon emission tomography (SPECT) and positron emission tomography (PET), 3D virtual tissue models generated from these modalities, optical imaging within the skill of the art. Intra-operative modalities can be fluoroscopy, infrared, X-rays, optical imaging or any other imaging modality compatible with the imaging modality used during the planning within the skill of the art. However, other imaging techniques commonly known in the art are also possible. The planning and the intra-operative modalities are not required to be different from each other. An example of such an anatomical landmark is an angular point visible on the outline of the extremity of a radius, described in the anatomy literature under the naming "styloid process of the radius". That landmark can be identified on a CT scan as planning modality and on a fluoroscopic scan as intra-operative modality.

The fitting tool of the devices of the present invention further comprise a supporting means. These supporting means are features on the patient-specific device onto which the different elements of the fitting tool, i.e. the functional alignment element and/or the patient-specific landmarking elements are positioned. As further shown herein, the supporting means comprising the alignment and/or landmarking features can be either integrated or removable from the patient-specific device.

As detailed above, the purpose of the functional alignment element is to place the device in the correct orientation in which the positional check can be made. The shape or functionality of the functional alignment element allows the user to define precisely the correct direction and angle at which the device is visualized directly or in the image taken by an imaging apparatus. The functional alignment element(s) can be a feature which is visible on the image but can also be radio-opaque so that when an imaging device is used, the device can be aligned through this element with the beam of the imaging system. The one or more functional alignment elements can be solid parts or devices that emit signals. An example of such a signal emitting device can be a laser diode. In particular embodiments, the diode is placed on the device so that only when the device is put in the correct alignment with the direction that the image is taken by the imaging device the laser appears as a dot.

The landmarking and/or alignment features of the fitting tool according to the invention can be part of the device or can be mechanisms that are to be used with the device in the location to be assessed. An advantage of a system which exists out of different parts, e.g. the features are separate parts which can be mounted in a particular direction, is that it makes it possible to use the same pointing/alignment feature(s) with different fitting devices. Indeed, in particular embodiments, the landmarking and/or alignment features are removable; as indicated above, the fitting tool comprises supporting means, which in particular embodiments are removable and adjustable so that the landmarking and/or alignment mechanism can be inserted in a specific position and location. In alternative embodiments, the landmarking and/or alignment features (and the corresponding supporting means) are an integral part of the fitting tool. More particularly, they can be produced as one piece within the fitting tool. In particular embodiments the supporting means are cylinders and the landmarking and/or alignment feature is a (standard) pin that is to be inserted therein. In further particular embodiments, the supporting means are slots in which a (standard) pointing mechanism is inserted in a unique way. Different embodiments are envisaged in the context of the invention, as long as the pointing features can be fixed in the fitting tool in a patient-specific orientation in order to adequately represent the correct relative position of the alignment feature and the landmarks.

It will be clearly understood from the above that the exact shape and size of the alignment and landmarking elements are not critical, provided that they can be correctly positioned to reflect the correct position of the patient-specific device.

Thus, alignment features can be of any shape as long as their orientation can be made to correlate from the user's perspective with a specific orientation of the device.

The patient-specific landmarking elements can be any mechanism that visualised through a given imaging modality with a given angle correlates with the identified landmarks. The term "correlates with" in the context of the landmarking elements in practice typically means "aligns with". More particularly this implies that the landmarking elements either point to, or have one or more visual aspects corresponding to, or can be aligned with the contour or part of the contour of the landmark on the anatomy of interest. Examples of such mechanisms can be, but are not limited to: hands, beams, extensions of the fitting device, or signal emitting devices. An example of a signal emitting device can be a laser diode emitting a laser beam that is only visible with the use an infrared imaging device. The common features among the different envisaged embodiments are that they can be correlated to the landmarks identified on the planning modality and that they can be mounted on the patient-specific device to attain fitting detection accuracy in the order of magnitude of the resolution of the used imaging modalities. These features can be radio-opaque so that when a radiographic imaging device is used, subcutaneous anatomical landmarks can also be identified. There are numerous ways to correlate e.g. pointing features and landmarks. In some embodiments, a point defined on the landmarking feature will superpose with a point of a landmark identified on the intra-operative modality when the patient-specific device is placed correctly. In some embodiments, a curve defined by the landmarking feature will align with a curve of a landmark identified on the intra-operative modality when the patient-specific device is placed correctly. In some embodiments, a segment on the landmarking feature has a specific orientation relative to a feature of a landmark on the anatomy. In some embodiments, the landmarking feature fits specifically on the contour line of a bone outline or a part of the bone such as a specific anatomical feature on the bone, when the device is placed in the fit position. It is noted that this alignment is to be considered as viewed/recorded by the imaging device and thus refers to a visual alignment or correspondence rather than a physical alignment (though a physical alignment is not excluded).

In particular embodiments, the fitting tools of the present invention can further comprise one or more surfaces which are patient-specific. More particularly, it is envisaged that the one or more landmarking features can be connected to a support (i.e. other than that used for the patient-specific device), which further ensures their correct position. In particular embodiments, the landmarking features are "hands" and the fitting tool comprises one or more "hand holders" which can support the hands and optionally comprise a (patient-specific) surface. The patient-specific surface can be a surface on the device or on the patient anatomy. The support structures or hand holders can be an integral part of the fitting device and can be connected to the landmarking features and/or the functional alignment element. In particular embodiments, the hand holders are designed to specifically fit the hands of the fitting tool (such that they have a specific orientation). In particular embodiments, the hand holders are separate components which can be positioned by the user upon positioning the patient-specific device of the invention.

Thus in one aspect the invention provides patient-specific surgical, therapeutic or diagnostic devices, which in addition to comprising a patient-specific surface which is complementary to least part of a chosen anatomy of a patient, further comprise a fitting tool for ensuring the correct fit of said device onto the chosen anatomy of said patient. More particularly, the fitting tool comprises supporting means for connection of the fitting tool to the rest of the patient-specific device and (i) at least one functional alignment element, for correctly aligning said device with the user's line of sight or with a medical imaging apparatus, and (ii) one or more landmarking elements which line up with one or more predetermined patient-specific landmarks on said chosen anatomy when said device is in said correct position.

In particular embodiments, the patient-specific devices according to the present invention additionally comprise means such as tunnels, loops, slots or dents for providing specific functionalities onto said device.

The functional alignment elements are typically chosen from pins, wires, columns, cubes or any other type of geometrical elements that allow accurate alignment.

The landmarking elements are typically chosen from pointers, pins, arms, hands, wires or any other type of geometrical elements that allow accurate landmarking.

The devices of the present invention are characterized by the presence of a fitting tool. Typically the fitting tools of the devices according to the present invention are designed such that one or more of the predetermined patient-specific landmarks on the chosen anatomy is a crest, a concavity, a convexity, a peak or a tuberosity on the outline of a bone or on a specific anatomical feature of the bone.

In particular embodiments, the fitting tools of the devices according to the present invention are designed such that at least one of the patient-specific landmarking elements is longitudinal and, when the patient-specific device is placed in the correct position, lines up with a specific point on a patient-specific landmark (in the image of the imaging device).

In particular embodiments, the fitting tools of the devices according to the present invention provide that at least one of said patient-specific landmarking elements lines up with part of the contour of a bone of said patient, when the device is placed in the correct position on said chosen anatomy. Alternatively, the patient-specific landmarking elements may also line up with part of the contour of an anatomical feature on a bone of said patient.

In particular embodiments, the fitting tools of the devices according to the present invention provide that, when the device is placed on the correct position of the chosen anatomy, at least one of said patient-specific landmarking elements lines up with an axis parallel or perpendicular to said chosen anatomy.

For correctly positioning a patient-specific device onto the patient concerned, the surgeon can typically only rely on his visual senses and his touch to control the correct fit of the device. The patient-specific devices according to the present invention only correctly fit in a single position, but some factors can cause the surgeon to err. The surgeon may be misguided to think that the device is in the correct fit position while it is not. This can be caused for instance by a lack of visibility of the bone and/or the device upon placement, a lack of experience of the surgeon, a lack of precision in the fitting surface etc.

The present invention allows the user to check the placement of the device using preoperatively identified patient-specific anatomical landmarks. The advantage of this invention is that it offers the user a way to check the correct fit of the device intra-operatively with a high precision.

A further aspect of the invention thus relates to a method for validating the correct position of a patient-specific device on a chosen anatomy of the human body, the method comprising the steps of:

positioning the patient-specific device on said chosen anatomy of the human body, wherein said patient-specific device comprises;

(a) a patient-specific surface being complementary with at least part of the body or bone structure of said patient at said chosen anatomy; and;

(b) a fitting tool comprising supporting means for connection to said patient-specific device and (i) at least one functional alignment element, for correctly aligning said device with the user's line of sight or with a medical imaging apparatus, and (ii) one or more patient-specific landmarking elements, which line up with one or more predetermined patient-specific landmarks on said chosen anatomy when said device is in said correct position;

aligning said functional alignment element with the user's line of sight or with a medical imaging apparatus, while maintaining said device in said position on said chosen anatomy; and checking whether said one or more patient-specific landmarking elements line up with said predetermined patient-specific landmark on said chosen anatomy, thereby validating the correct position of a patient-specific device on a chosen anatomy of the human body.

Where the patient-specific device is correctly positioned (i.e. in the pre-determined position) on the chosen anatomy, the one or more patient-specific landmarking elements will align with the corresponding landmarks. The fitting tool can then optionally be removed, and the surgery continued with the patient-specific device in place. Where the landmarking elements of the device do not align with the corresponding landmarks after aligning the device (positioned on the chosen anatomy) with the user's line of sight or the medical imaging device, this implies that the patient-specific device is not positioned completely in accordance with pre-operative planning. The reasons for this may be multiple, e.g. (minor) errors in planning, (minor) errors in manufacture of the patient-specific device etc. It can then be decided to adjust the position of the device on the bone. However, in particular embodiments, this may lead to rejection of the patient-specific device.

The direction in which the alignment of said functional alignment element of the device after positioning of the device on the patient occurs is dependent on the type of functional alignment element. The alignment can occur such that the direction that the image is taken by the device (or the user's line of sight) is exactly perpendicular to the alignment feature (in the same direction). For instance, when the alignment feature is a pin-like structure, the required alignment can be such that the resulting image of the alignment feature by the user or the device is a circle (i.e. the pin viewed from the top). Or the required alignment can be the positioning of the line of sight or image from any other angle, for example, if the alignment feature provides a certain signal under that angle. More particularly, in the methods according to the present invention the alignment of said functional alignment element with the user's line of sight or with a medical imaging apparatus comprises positioning said alignment feature parallel with the direction in which the image is taken by the device. The alignment can occur either by moving the medical imaging apparatus or the user's sight into the correct alignment position or by moving the patient-specific device (and thereby also the patient's anatomical part on which it is positioned) into the correct alignment position.

Once the device is correctly aligned with the imaging device (or the direction of sight of the user) using the alignment features, it is possible for the user to verify the correct position of the device on the anatomical part based on the landmarking features. Indeed, provided the device is correctly aligned with the user's view and/or the imaging device, the landmarking features of the fitting tool should correspond with the landmarks on the anatomical part. In particular embodiments, this implies that the landmarking features are aligned with (e.g. point directly to, or are in parallel with) the corresponding landmarking feature. Where the landmarking features do not correspond to the corresponding landmarks, this implies that the device is not completely correctly positioned on the anatomical part.

In particular embodiments of the methods according to the present invention the step of checking whether said one or more patient-specific landmarking element(s) line up with said predetermined patient-specific landmark(s) is performed by imaging said device using a radiographic scan and/or an ultrasound scan at a specific angle determined by said alignment feature.

Typically, in the devices according to the invention, the patient-specific fitting tool, comprising a functional alignment element and a patient-specific landmarking element, is designed and positioned on the patient-specific device on the basis of patient-specific information obtained pre-operatively.

A further aspect of the invention provides a method for manufacturing a patient-specific device comprising a fitting tool, said method comprises the steps of:
obtaining patient-specific information regarding the chosen anatomy of the human body onto which the patient-specific device is to be positioned;
using said patient-specific information for designing said patient-specific guide such that said guide is provided with:
(a) a patient-specific surface being complementary with at least part of the body or bone structure of said patient; and;

(b) a patient-specific fitting tool comprising supporting means for connection of said fitting tool to said patient-specific device and
(i) at least one functional alignment element, for aligning said device with the user's line of sight and/or with a medical imaging apparatus, and
(ii) one or more patient-specific landmarking elements, which line up with one or more predetermined patient-specific landmarks on said chosen anatomy when said device is in said correct position; wherein the position of said landmarking elements with regard to said functional alignment element is patient specific; and
manufacturing said patient-specific device.

In particular embodiments of the manufacturing method according to the present invention the step of obtaining patient-specific information comprises performing a radiographic scan, a MRI scan and/or a CT scan.

The step of obtaining patient-specific information regarding the chosen anatomy of the human body typically includes identifying landmarks which can be used to determine the correct position of the device. This implies that a landmarking element can be designed based thereon which will guarantee that, when the landmarking element and the landmark correspond, the device is correctly positioned.

In particular embodiments of the manufacturing method according to the present invention the manufacturing step is ensured by additive manufacturing.

In a further particular embodiment, Additive Manufacturing (AM) techniques are used for manufacturing the surgical fixtures according to the invention, or parts thereof. AM techniques are particularly useful to manufacture patient-specific contact surfaces, or to produce the surgical fixtures in one piece. As an example, the manufacturing of medical-image-based patient-specific surgical instruments via AM is described in U.S. Pat. No. 5,768,134 (Swaelens et al). AM can be defined as a group of techniques used to fabricate a tangible model of an object typically using three-dimensional (3-D) computer aided design (CAD) data of the object. Currently, a multitude of Additive Manufacturing techniques is available, including stereolithography, Selective Laser Sintering, Fused Deposition Modelling, foil-based techniques, etc.

Selective laser sintering uses a high power laser or another focused heat source to sinter or weld small particles of plastic, metal, or ceramic powders into a mass representing the 3-dimensional object to be formed.

Fused deposition modelling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The devices according to the present invention may be manufactured in different materials. Typically, only materials that are biocompatible (e.g. USP class VI compatible) with the animal or human body are taken into account. Preferably the surgical fixture is formed from a heat-tolerable material allowing it to tolerate high-temperature sterilization. In the case selective laser sintering is used as an AM technique, the surgical template may be fabricated from a polyamide such as PA 2200 as supplied by EOS, Munich, Germany or any other material known by those skilled in the art may also be used.

The present invention is hereafter exemplified by the illustration of particular, non-limiting examples.

EXAMPLES

Example 1

Figure 1A:
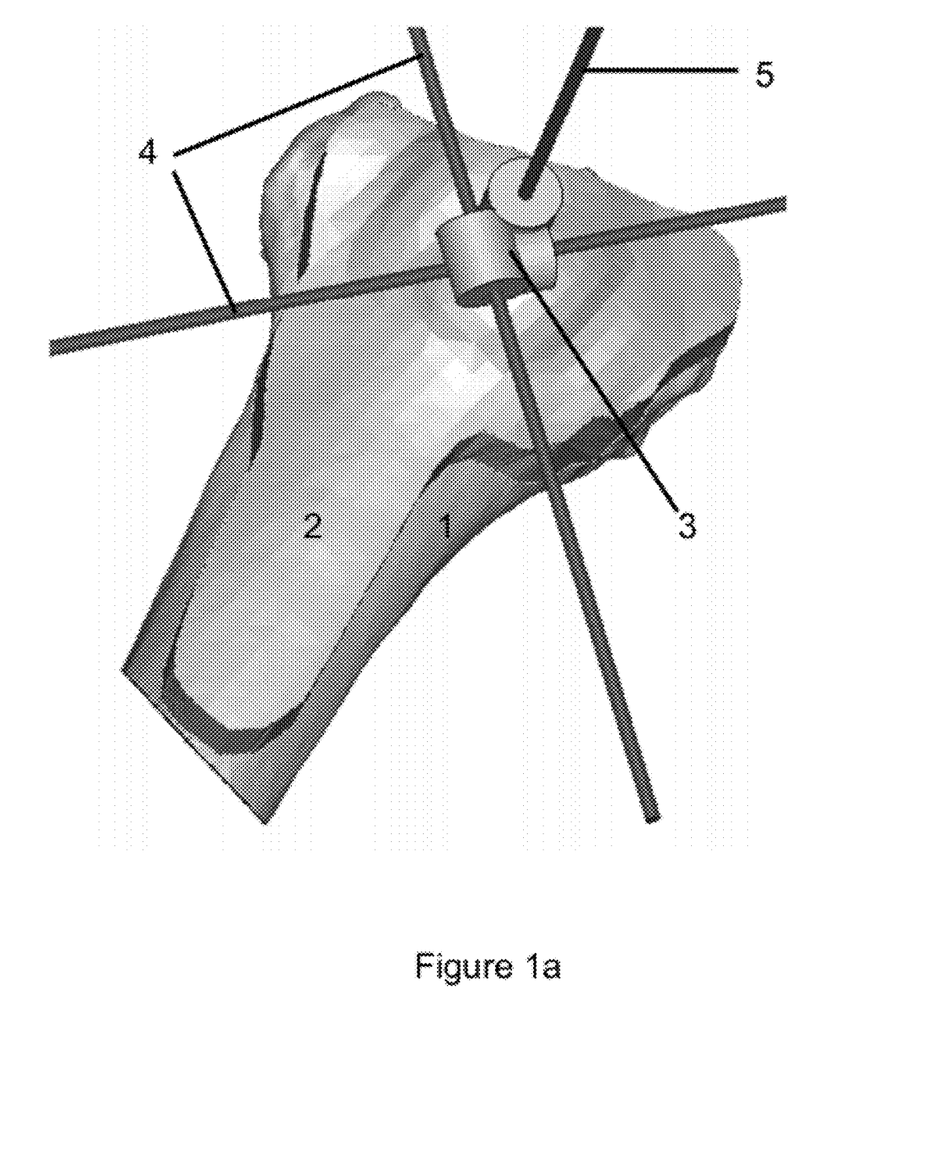

This example describes a specific but non-limiting embodiment of the patient-specific device according to the present invention. As shown in FIG. 1a a patient-specific device (2) is provided an anatomical part (1) of a patient the radius in the present case. The patient-specific device (2) is provided with a patient-specific surface (not visible) a fitting tool (3) comprising a functional alignment element (5), and two patient-specific landmarking elements (4). The patient-specific landmarking elements (4) are according to the present embodiment made of 2 metal wires of 1.25 mm diameter inserted in provided holes on the device that are visible on a fluoroscopy scan. One extra metal pin of 1.25 mm diameter is used as functional alignment element (5) for the visual alignment. The supporting element comprises in the present embodiment three cylinders with tunnels in the center where the pins can be inserted through and supported. Although the supporting means are shown with cylindrical shapes here, they can be any shape (block, sphere etc) that can hold pins in place with features such as tunnels, dents, loops, etc.

The control of the positioning of the patient-specific device (2) can be assessed when the functional alignment element (5) is aligned with the line of sight of the user or medical imaging unit such as a fluoroscope. In that position only is the tip of the metal pin visible to the user.

Figure 1B:
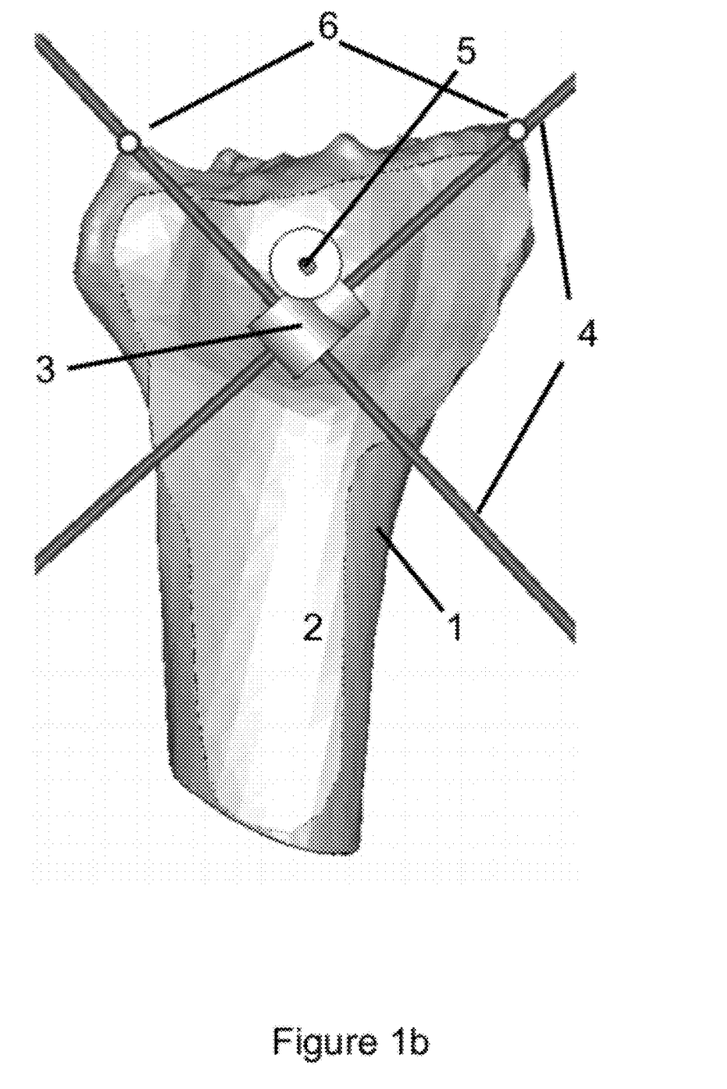

When the patient-specific device (2) is aligned and in the correct position on the bone, the two patient-specific landmarking elements (4) are visible on the fluoroscope and are intersecting the contour of the bone at the pre-identified landmarks (6), such as shown in FIG. 1b. In this case the device is fitting on a radius; the landmarks are the process of the radius (dots in FIG. 1b).

Figure 1C:
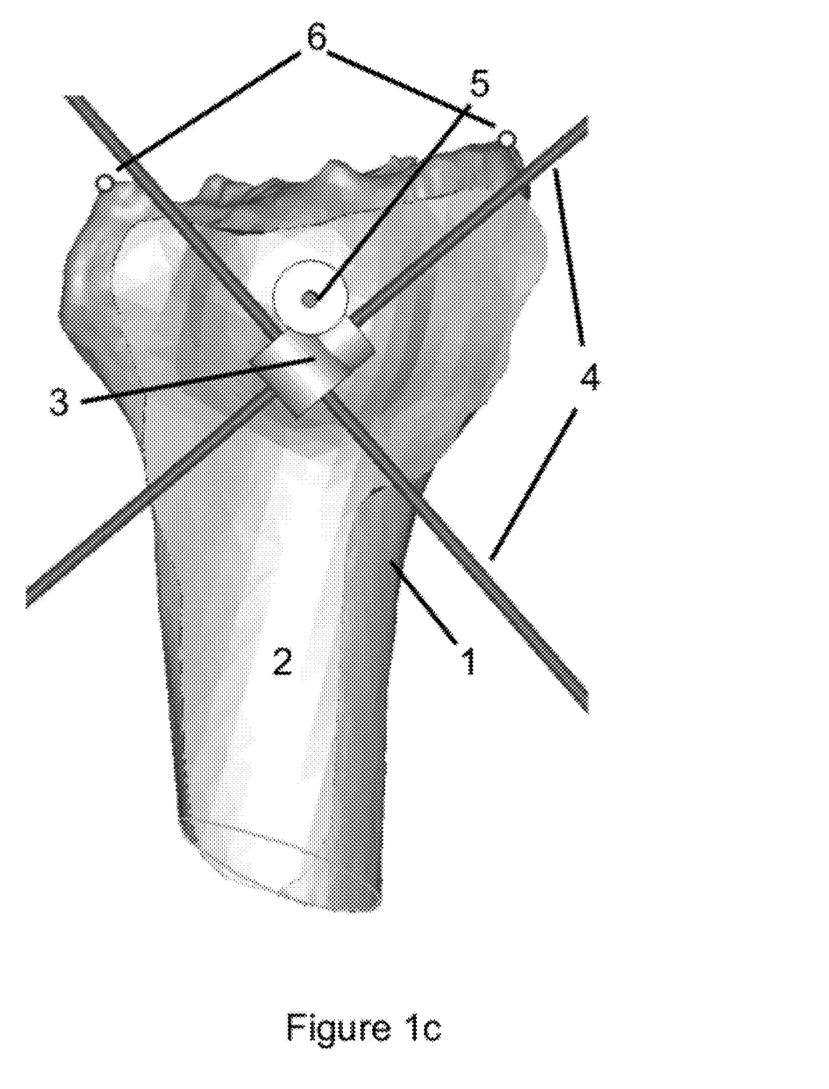

Only in that particular position will the patient-specific landmarking elements (4) cross the landmarks (6), a problem in the position of the patient-specific device (2) will result in a non-correlation of the patient-specific landmarking elements (4) with the landmarks, as shown in FIG. 1c.

Example 2

Figure 2A:
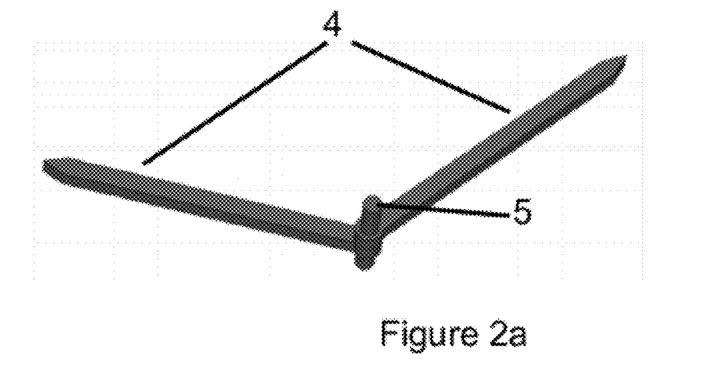
Figure 2B:
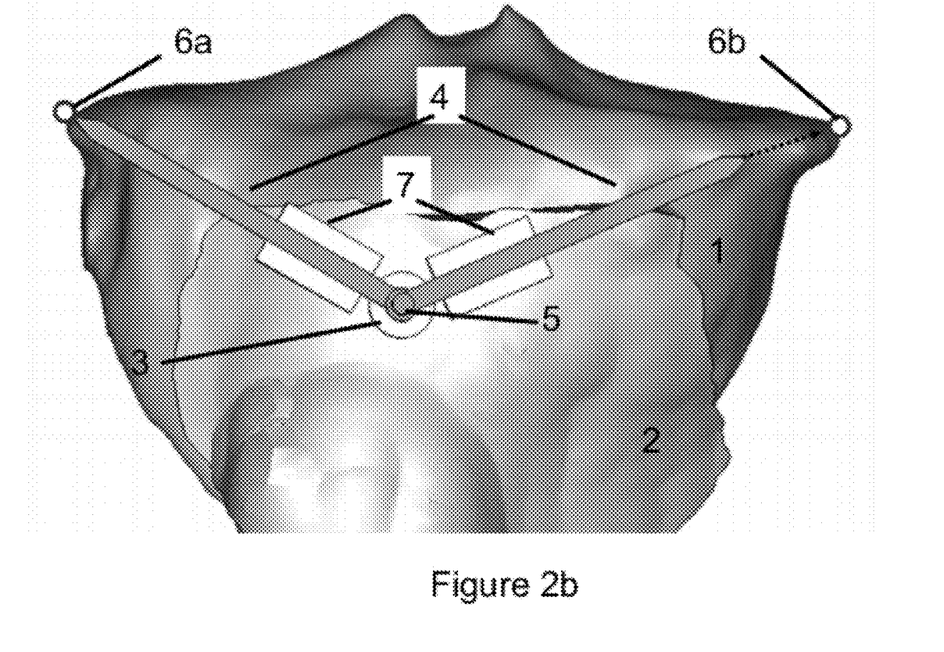
Figure 2C:
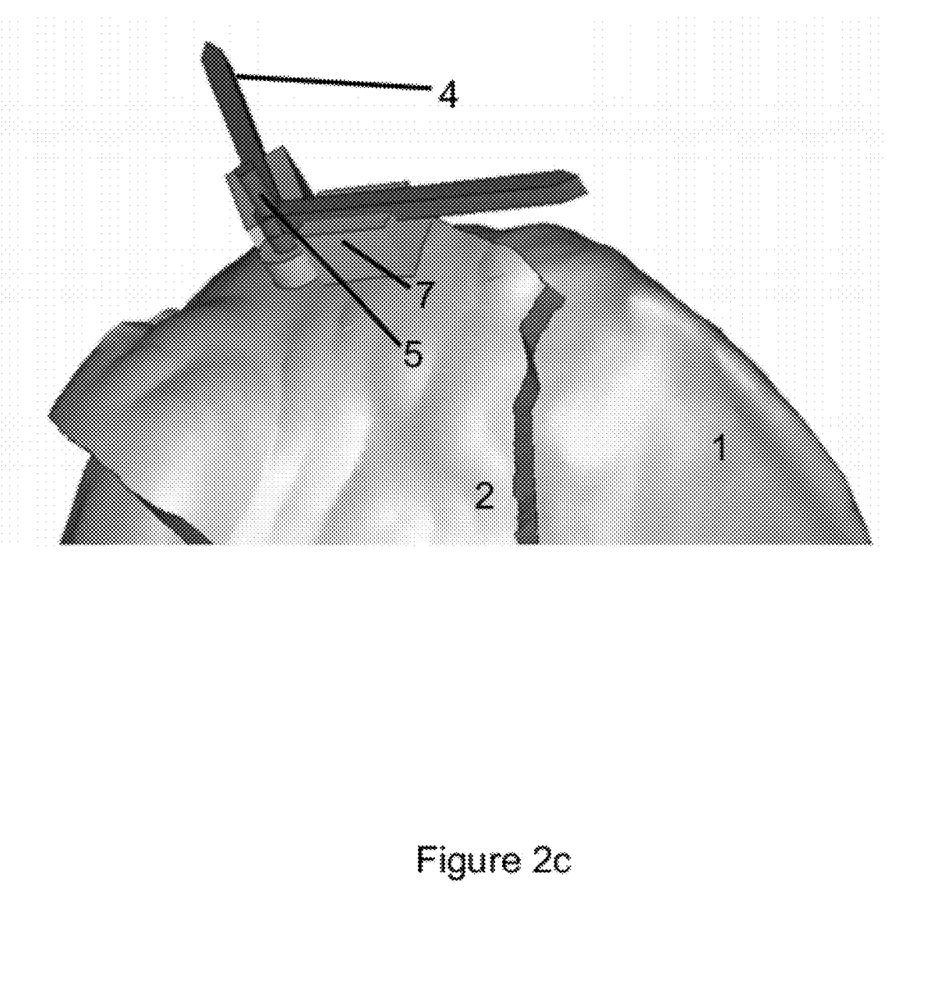

This example illustrated by FIGS. 2a-c, describes a specific but non-limiting embodiment of the patient-specific device according to the present invention. As shown in FIG. 2b a patient-specific device (2) is provided on an anatomical part (1) of a patient, i.e. the tibia in the present case.

The patient-specific device (2) is provided with a patient-specific surface (not visible), which fits on the tibia (1).

The device further comprises a fitting tool (3) comprising a functional alignment element (5), and two patient-specific landmarking elements (4). The patient-specific landmarking elements (4) are according to this embodiment two hands rotating around a central axis, the central axis being the functional alignment element (5).

The fitting tool (3) is removable (see FIG. 2a) and it can be metallic, plastic or any material that is safe to be used in surgery. The material can be radio-opaque or not.

Once positioned in the provided slot on the fitting tool (3), the hands of the fitting tools (3) are positioned in the hand holders (7) and the central axis is aligned with the user's line of sight or with the medical imaging unit such as a fluoroscope. If the device is correctly positioned, the pointing extremities of the hands will point directly at the predetermined anatomical landmarks (6). Here the landmarks are the medial and lateral extremities of the tibial plateau in the AP plane.

Example 3

Figure 3A:
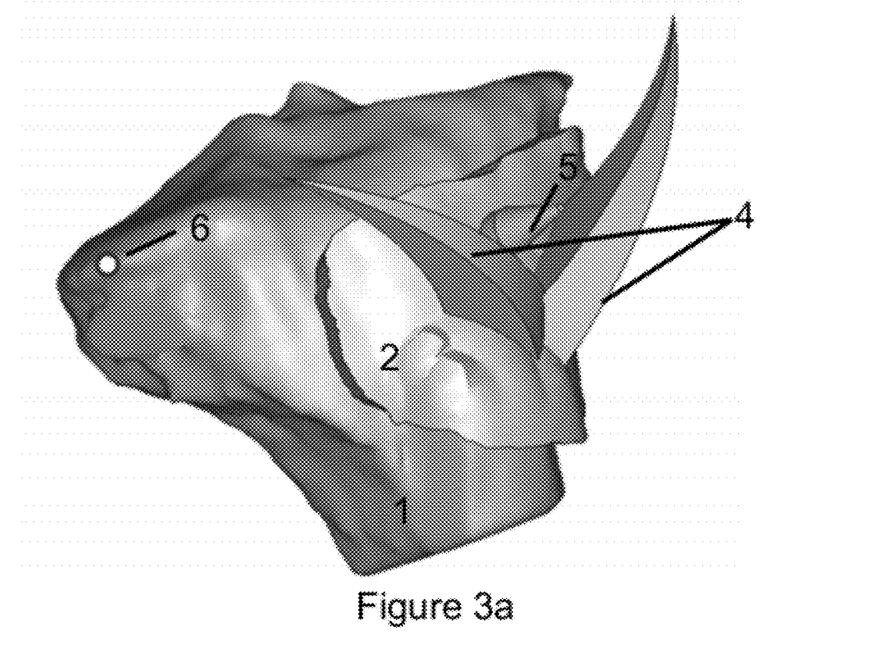

This example describes a specific but non-limiting embodiment of the patient-specific device according to the present invention. As shown in FIG. 3a a patient-specific device (2) is provided an anatomical part (1) of a patient, the tibia in the present case. The patient-specific device (2) is provided with a patient-specific surface (not visible) and the fitting tool comprises an individual functional alignment element (5) and two patient-specific landmarking elements (4) which are integrated into the patient-specific device (2). The patient-specific landmarking elements (4) have according to the present embodiment sharp pointing extremities and are outside the boundary of patient-specific device (2). The functional alignment element (5) comprises a cone with a flattened head. Aligning the device in the line of sight is done by centering of the contour of the flat surface relatively to the contour of the cone basis. In the aligned position the central axis of the alignment feature here is equal to the line of sight. If the landmarks (6) are not visible during surgery, the hands are made radio-opaque to be visible on an intra-operative imaging modality.

Figure 3B:
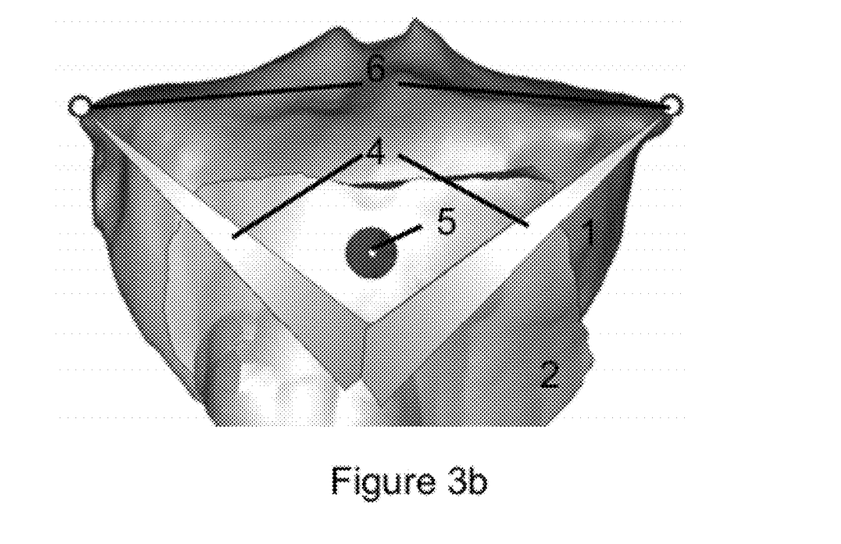

The edge of the extremities of the patient-specific landmarking elements (4) can be seen as points. When the device is placed in the correct position and viewed under the defined angle, these landmarking elements points superpose with the identified anatomical landmarks. In this embodiment the landmarks (6) are the medial and the lateral extremities of the tibial plateau in the AP plane. When the device is not viewed under the correct angle, the edges of the pointing features are not superimposed on the identifiable anatomic landmarks, as shown in FIG. 3b.

Example 4

Figure 4A:
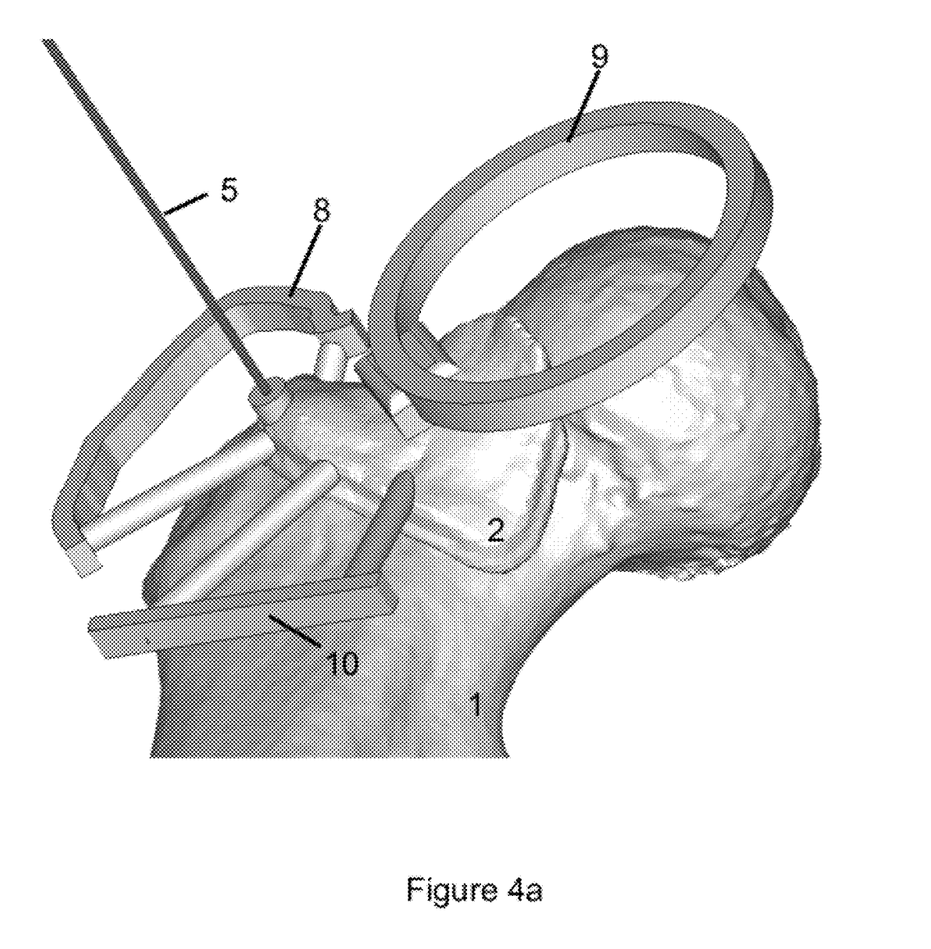
Figure 4B:
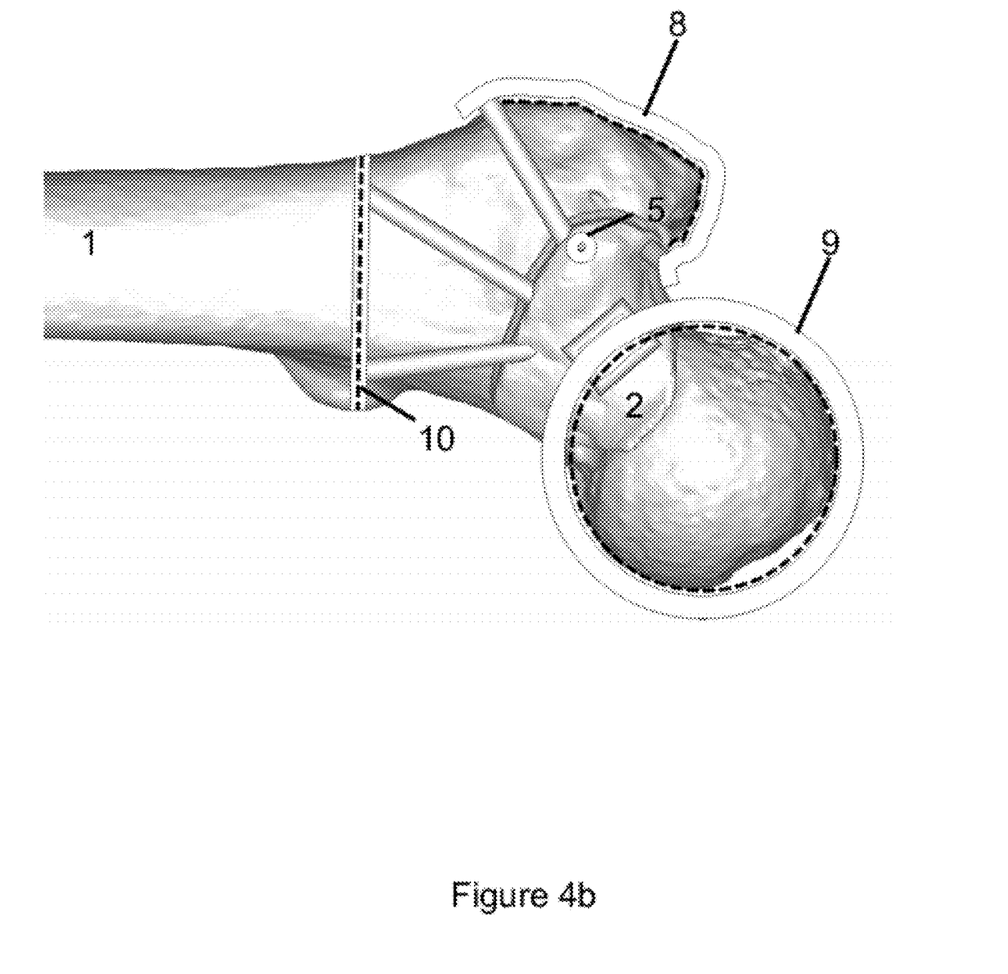

This example describes a specific but non-limiting embodiment of the patient-specific device according to the present invention. As shown in FIG. 4a a patient-specific device (2) is provided an anatomical part (1) of a patient the femur in the present case. The patient-specific device (2) is provided with a patient-specific surface (not visible) a fitting tool (3) comprising a functional alignment element (5), and patient-specific landmarking elements (8, 9, 10). Three examples of possible patient-specific landmarking elements (8, 9, 10) are provided in the present example. One type of patient-specific landmarking element (9) allows for a correlation between the anatomical landmark of spherical shape of the head of the femur and the ring shape of the patient-specific landmarking element. Another type of patient-specific landmarking element (8) allows to control the correct positioning of the device by ensuring that the outline of the patient-specific landmarking element visually follows the outline of the bone when the device is in the correct position and well aligned with the line of sight. The third type of patient-specific landmarking element (10) correlates with the thickness of the bone. The device is correctly positioned when the two ends of the suspended beam of the pointing feature are correlating to the outline of the bone.

Also other types of correlations between the landmarks and the patient-specific landmarking elements are possible. The patient-specific landmarking elements can be radioopaque depending on the requirements for the procedure.

The invention claimed is:

1. A method for validating a correct position of a patient-specific device on an anatomical part of the human body, the method comprising:
positioning the patient-specific device on the anatomical part, wherein the patient-specific device comprises:
a patient-specific surface configured to be complementary with at least a portion of the anatomical part;
a functional alignment element configured for optically aligning the device; and
a patient-specific landmarking element configured to align with a predetermined anatomical landmark on the anatomical part when the patient-specific device is in the correct position,
wherein the predetermined anatomical landmark is a visible, physical feature of the anatomical part when the patient-specific device is in the correct position,
and wherein the patient-specific landmarking element is a beam configured to correlate with a width of the predetermined anatomical landmark;
aligning the functional alignment element; and
checking whether the patient-specific landmarking element aligns with the predetermined anatomical landmark on the anatomical part in order to validate the correct position of the patient-specific device on the anatomical part.

2. The method of claim 1, wherein the anatomical part is a bone, and the visible, physical feature is one of a crest, a concavity, a convexity, a peak, or a tuberosity on the surface of the bone.

3. The method of claim 1, wherein the patient-specific landmarking element is longitudinal and configured to align with a specific point on the predetermined anatomical landmark.

4. The method of claim 3, wherein the anatomical part is a bone.

5. The method of claim 1, wherein aligning the functional alignment element is performed with a user's line of sight.

6. The method of claim 1, wherein aligning the functional alignment element is performed with a medical imaging apparatus.

7. The method of claim 6, wherein the medical imaging apparatus is one of a CT scan apparatus, an X-ray scan apparatus, an ultrasound apparatus, or an MRI apparatus.

8. The method of claim 1, wherein the patient-specific device further comprises: a fitting tool configured to attach to the patent-specific device and to support the functional alignment element and the patient-specific landmarking element.

9. The method of claim 1, wherein the functional alignment element is one of a pin, a rod, a wire, or a cone.

10. The method of claim 1, wherein the patient-specific surface was additively manufactured.

11. A method for validating a correct position of a patient-specific device on an anatomical part of the human body, the method comprising:
positioning the patient-specific device on the anatomical part, wherein the patient-specific device comprises:
a patient-specific surface configured to be complementary with at least a portion of the anatomical part;
a functional alignment element configured for optically aligning the device; and
a patient-specific landmarking element configured to align with a predetermined anatomical landmark on the anatomical part when the patient-specific device is in the correct position,
wherein the predetermined anatomical landmark is a visible, physical feature of the anatomical part when the patient-specific device is in the correct position,
and wherein the patient-specific landmarking element defines a curve configured to align with a portion of a contour of the predetermined anatomical landmark;
aligning the functional alignment element; and
checking whether the patient-specific landmarking element aligns with the predetermined anatomical landmark on the anatomical part in order to validate the correct position of the patient-specific device on the anatomical part.

12. The method of claim 11, wherein the anatomical part is a bone, and the visible, physical feature is one of a crest, a concavity, a convexity, a peak, or a tuberosity on the surface of the bone.

13. A method for validating a correct position of a patient-specific device on an anatomical part of the human body, the method comprising:
positioning the patient-specific device on the anatomical part, wherein the patient-specific device comprises:
a patient-specific surface configured to be complementary with at least a portion of the anatomical part;
a functional alignment element configured for optically aligning the device; and
a patient-specific landmarking element configured to align with a predetermined anatomical landmark on the anatomical part when the patient-specific device is in the correct position,
wherein the predetermined anatomical landmark is a visible, physical feature of the anatomical part when the patient-specific device is in the correct position,
and wherein the patient-specific landmarking element is a ring configured to correlate with an outline of the predetermined anatomical landmark;
aligning the functional alignment element; and
checking whether the patient-specific landmarking element aligns with the predetermined anatomical landmark on the anatomical part in order to validate the correct position of the patient-specific device on the anatomical part.

14. The method of claim 13, wherein the anatomical part is a bone, and the visible, physical feature is one of a crest, a concavity, a convexity, a peak, or a tuberosity on the surface of the bone.

* * * * *